United States Patent
Kim et al.

(10) Patent No.: US 10,532,658 B2
(45) Date of Patent: Jan. 14, 2020

(54) HEALTH MEASUREMENT SYSTEM FOR VEHICLE'S DRIVER AND WARNING METHOD USING THE SAME

(71) Applicants: HYUNDAI MOTOR COMPANY, Seoul (KR); KIA MOTORS CORPORATION, Seoul (KR)

(72) Inventors: Kye Yoon Kim, Gunpo-si (KR); Jung Mi Park, Anyang-si (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 20 days.

(21) Appl. No.: 15/857,395

(22) Filed: Dec. 28, 2017

(65) Prior Publication Data

US 2019/0092167 A1    Mar. 28, 2019

(30) Foreign Application Priority Data

Sep. 28, 2017  (KR) .................. 10-2017-0126190

(51) Int. Cl.
| | |
|---|---|
| *B60K 28/06* | (2006.01) |
| *G08B 21/06* | (2006.01) |
| *A61B 5/18* | (2006.01) |
| *B60W 40/08* | (2012.01) |

(52) U.S. Cl.
CPC .............. *B60K 28/066* (2013.01); *A61B 5/18* (2013.01); *G08B 21/06* (2013.01); *B60W 2040/0827* (2013.01); *B60W 2040/0836* (2013.01); *B60W 2040/0872* (2013.01)

(58) Field of Classification Search
CPC ........ B60K 28/066; B60W 2040/0827; B60W 2040/0836; B60W 2040/0872; A61B 5/18; G08B 21/06

USPC .......................................................... 340/576
See application file for complete search history.

(56) References Cited

U.S. PATENT DOCUMENTS

| | | | | |
|---|---|---|---|---|
| 2008/0227466 | A1* | 9/2008 | Rabanne | G01S 5/0027 |
| | | | | 455/456.1 |
| 2010/0030434 | A1* | 2/2010 | Okabe | A61B 5/165 |
| | | | | 701/48 |
| 2014/0218187 | A1 | 8/2014 | Chun et al. | |

FOREIGN PATENT DOCUMENTS

| | | |
|---|---|---|
| JP | 2008-217274 A | 9/2008 |
| JP | 2013-001240 A | 1/2013 |
| JP | 2015-141536 A | 8/2015 |
| KR | 10-2014-0096609 A | 8/2014 |
| KR | 10-2015-0078476 A | 7/2015 |
| KR | 10-2015-0114781 A | 10/2015 |
| KR | 10-1646418 B1 | 8/2016 |

* cited by examiner

*Primary Examiner* — Benyam Haile
*Assistant Examiner* — Mancil Littlejohn, Jr.
(74) *Attorney, Agent, or Firm* — Morgan, Lewis & Bockius LLP

(57) ABSTRACT

A health measurement system for a vehicle driver and a warning method using the same are disclosed. The health measurement system includes an Internet of Things (IoT) device and a controller. The controller performs health scanning of a driver through the IoT device, and informs the driver of a result of the health scanning. The controller determines a necessary condition of the health scanning of the driver by analyzing traveling environment information, and performs the health scanning only when the necessary condition of the health scanning is satisfied.

18 Claims, 4 Drawing Sheets

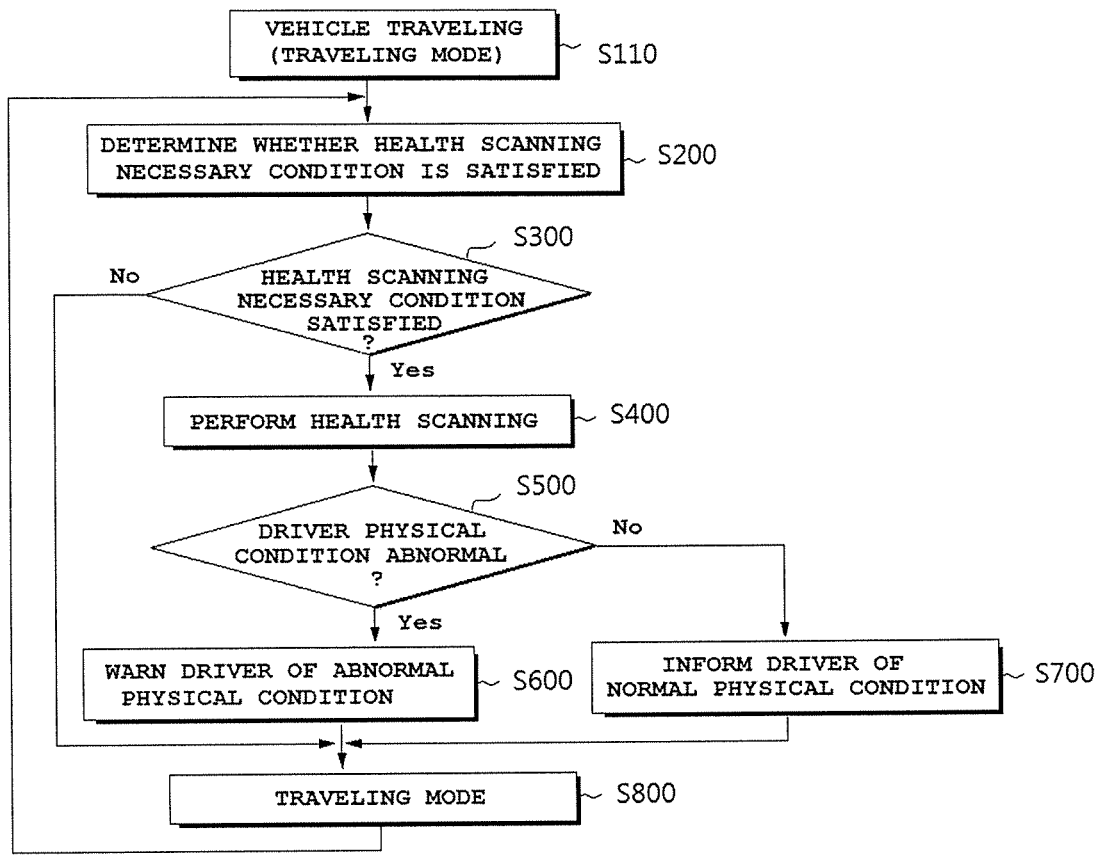

HEALTH MEASUREMENT SYSTEM FOR VEHICLE'S DRIVER AND WARNING METHOD USING THE SAME

This application is based on and claims the benefit of priority to Korean Patent Application No. 10-2017-0126190, filed on Sep. 28, 2017 with the Korean Intellectual Property Office, which is hereby incorporated by reference as if fully set forth herein.

TECHNICAL FIELD

The present disclosure relates to a vehicle, and more particularly to a heath measurement system for scanning a physical state of a driver of a vehicle before the vehicle starts driving or while the vehicle is in motion, and informing the driver of occurrence of an abnormal health condition, and a warning method using the same.

BACKGROUND

Generally, traffic accidents may occur due to various reasons, for example, careless driving of vehicle drivers or unexpected hazards caused by road conditions. In particular, the number of traffic accidents caused by drowsy driving is increasing every year. Most traffic accidents caused by drowsy driving may cause fatal accidents leading to human casualties, resulting in serious social problems.

The driver may perform drowsy driving caused by mental or physical fatigue, for example, lack of sleep, prolonged driving, driving on boring roads, traffic jams, etc.

For safe driving, it is necessary to check the driver's health condition in advance so as to prevent accidents caused by drowsy driving.

SUMMARY

Accordingly, the present disclosure is directed to a health measurement system for a driver of a vehicle and a warning method using the same that substantially obviate one or more problems due to limitations and disadvantages of the related art.

An object of the present disclosure is to provide a health measurement system for a vehicle's driver and a warning method using the same, which can determine whether the driver has a healthy condition appropriate for vehicle driving by scanning a physical condition of the driver at a proper time, and can warn the driver of his or her abnormal health condition when the healthy condition of the driver is not found, thereby arousing a driver's attention in safe driving.

Another object of the present disclosure is to provide a health measurement system of a vehicle driver which can scan a health condition of the driver only at a necessary time without performing repeated and unconditional health scanning.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

In accordance with another aspect of the present disclosure, a health measurement system for a driver of a vehicle includes: an ignition switch; a starter motor; an Internet of Things (IoT) device; and a controller communicatively connected to the IOT device and configured to determine a necessary condition of health scanning of the driver, and perform the health scanning according to a result of the determination; a starter relay configured to supply a battery voltage to the controller and the starter motor, in which the controller analyzes traveling environment information when the ignition switch is turned on, determines whether the necessary condition of the health scanning is satisfied, and performs the health scanning only when the necessary condition of the health scanning is satisfied.

The traveling environment information may include at least one of a date and time at which the vehicle starts ignition, an estimated driving time, a traveling time, a current time, a traveling route, and a traffic situation.

The IoT device may include at least one of a smartphone, a health band, and a smart watch.

When determining whether the necessary condition of the health scanning is satisfied, if any one of the traveling environment information is satisfied, a determination is made that the health scanning is needed, and if any one of the traveling environment information is not satisfied, a determination is made that the health scanning need not be performed.

The controller may interact with an ignition switch, and may determine whether the necessary condition of the health scanning is satisfied during ignition starting of the vehicle or during traveling of the vehicle.

If the necessary condition of the health scanning is satisfied, the controller may pre-inform the driver of the health scanning, and may then execute the health scanning for the driver.

The health scanning may be executed in consideration of at least one of the number of footsteps of the driver, a body temperature, a pulse rate, a heart rate, a fatigue level, and a sleep time record, which are stored in a telematics terminal or the IoT device.

The controller may determine whether a physical condition of the driver is normal or abnormal through an execution result of the health scanning.

The controller may visually or audibly display a result of the health scanning through the telematics terminal.

The display result of the health scanning may display at least one of the number of footsteps of the driver, a body temperature, a pulse rate, a heart rate, a fatigue level, and a sleep time record using numerals or symbols, and may include content for determining whether a health condition of the driver is normal or abnormal.

In accordance with another aspect of the present disclosure, a warning method using a health measurement system for a driver of a vehicle, the health measurement system including a controller and an Internet of Things (IoT) device that are communicatively connected each other, the warning method includes steps of: receiving, by the controller, an ignition start signal of the vehicle; analyzing, by the controller, traveling environment information, and determining whether a necessary condition of health scanning for the driver is satisfied; if the health scanning necessary condition is satisfied, executing, by the controller, the health scanning for the driver; determining, by the controller, whether a physical condition of the driver is normal or abnormal through an execution result of the health scanning; and if the physical condition of the driver is abnormal, displaying, by a telematics terminal of the vehicle, a warning message indicating the physical condition of the driver is abnormal, and if the physical condition of the driver is normal, displaying a message indicating the physical condition of the driver is normal.

The traveling environment information may include at least one of a date and time at which the vehicle starts ignition, an estimated driving time, a traveling route, and a traffic situation.

The IoT device may include at least one of a smartphone, a health band, and a smart watch.

The step of determining whether a necessary condition of the health scanning is satisfied may include: determining whether, from among the traveling environment information, at least one of a first condition in which a date is changed when the vehicle starts ignition, a second condition in which a predetermined time has elapsed after the vehicle stops ignition, a third condition in which the vehicle is scheduled to travel for at least a predetermined travel time, a fourth condition in which a section having less cognitive load or less stimulus is contained in the traveling route, and a fifth condition in which a congested section is contained in the traveling route is satisfied.

The determining whether the health scanning necessary condition is satisfied may include: if any one of the first to fifth conditions is satisfied, determining that the health scanning is needed; and if any one of the first to fifth conditions is not satisfied, determining that the health scanning need not be executed.

The health scanning may be executed in consideration of at least one of the number of footsteps of the driver, a body temperature, a pulse rate, a heart rate, a fatigue level, and a sleep time record, which are received from the IoT device.

The traveling environment information may be stored in a telematics terminal of the vehicle. The IoT device may communicate with the telematics terminal.

The step of displaying a warning message may include at least one of visually displaying the warning message through the telematics terminal and audibly displaying the warning message through the telematics terminal.

The step of displaying a warning message may include: displaying at least one of the number of footsteps of the driver, a body temperature, a pulse rate, a heart rate, a fatigue level, and a sleep time record using numerals or symbols, and including content for determining whether the physical condition of the driver is normal or abnormal.

The method may further include, prior to the step of executing health scanning of the driver, if the necessary condition of the health scanning is satisfied, pre-informing the driver of the health scanning.

In accordance with another aspect of the present disclosure, a warning method using a health measurement system of a driver of a vehicle, the health measurement system including a controller and a telematics terminal that are communicatively connected each other, the warning method includes: allowing the vehicle to operate in a traveling mode; determining, by the controller, whether a necessary condition of health scanning of the driver is satisfied by analyzing traveling environment information; if the necessary condition of the health scanning is satisfied, executing, by the controller, health scanning of the driver; determining, by the controller, whether a physical condition of the driver is normal or abnormal through an execution result of the health scanning; and if the physical condition of the driver is abnormal, displaying, by the telematics terminal, a warning message indicating the physical condition of the driver is abnormal, and if the physical condition of the driver is normal, displaying a message indicating the physical condition of the driver is normal.

The traveling environment information may include at least one of a traveling time, a current time, a traveling route, and a traffic situation.

The warning method further includes: after the step of displaying a warning message indicating the physical condition of the driver is abnormal or the step of displaying a message indicating the physical condition of the driver is normal, re-performing the step of determining whether a necessary condition of health scanning is satisfied.

The step of determining whether a necessary condition of health scanning is satisfied may include: determining whether, from among the traveling environment information, at least one of a first condition in which the vehicle travels for at least a predetermined time at night, a second condition in which the vehicle is scheduled to travel for at least a predetermined travel time, a third condition in which a section having less cognitive load or less stimulus is contained in the traveling route, and a fourth condition in which a congested section is contained in the traveling route is satisfied.

The step of determining whether a necessary condition of health scanning is satisfied may include: if any one of the first to fourth conditions is satisfied, determining that the health scanning is needed; and if any one of the first to fourth conditions is not satisfied, determining that the health scanning need not be executed.

The method may further include: prior to the step of executing health scanning of the driver, if the necessary condition of the health scanning is satisfied, pre-informing the driver of the health scanning.

It is to be understood that both the foregoing general description and the following detailed description of the present disclosure are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings:

FIG. 4 is a flowchart illustrating a warning method using a health measurement system for a vehicle driver according to another embodiment of the present disclosure.

DETAILED DESCRIPTION

Figure 1:
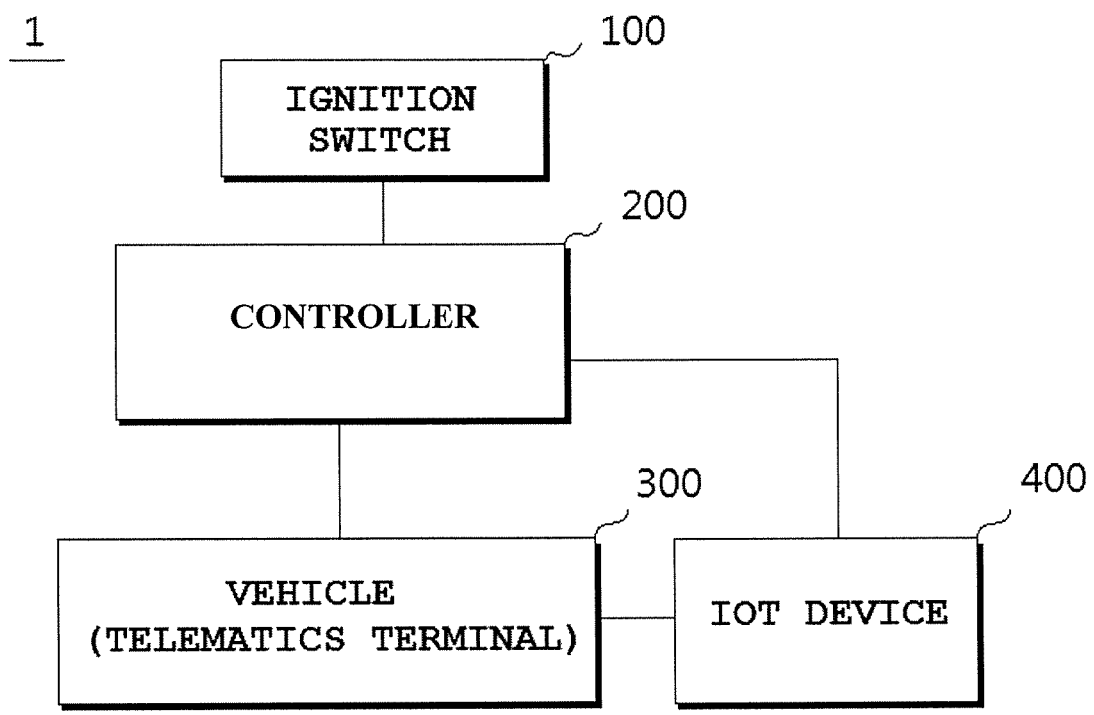
FIG. 1 is a block diagram illustrating a health measurement system for a vehicle driver according to an embodiment of the present disclosure.

Hereinafter, the embodiments will be clearly appreciated through the accompanying drawings and the following description thereof.

In the drawings, sizes and shapes of elements may be exaggerated, omitted or schematically illustrated for clarity and convenience. In addition, the size of each constituent element does not wholly reflect an actual size thereof. In addition, the same reference numerals designate the same constituent elements throughout the description of the drawings.

Figure 2:
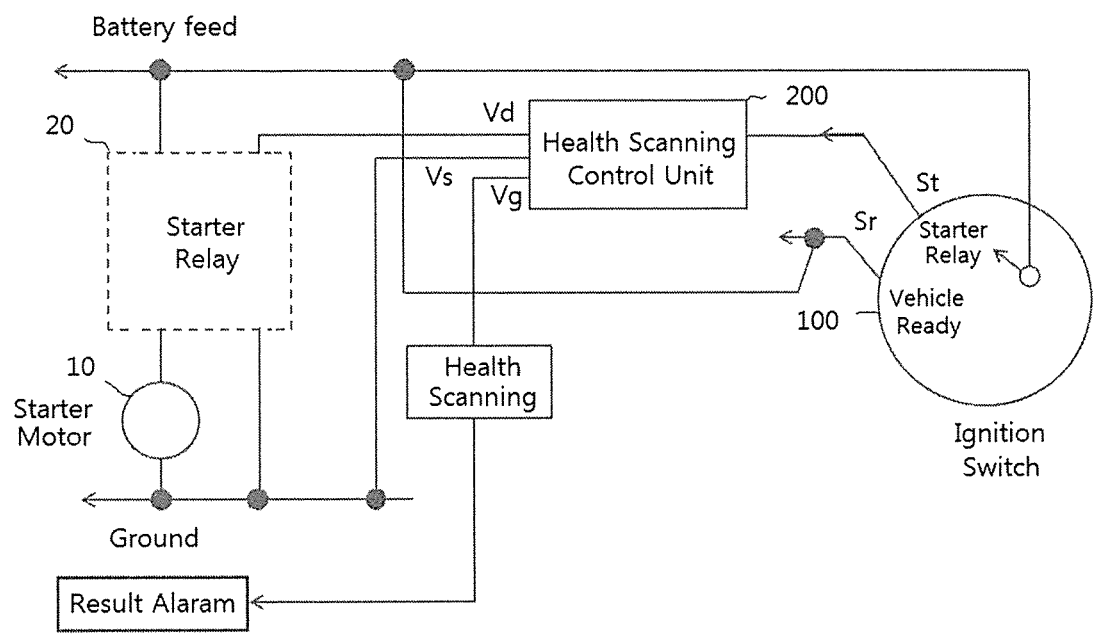
FIG. 2 is a circuit diagram illustrating constituent elements of the health measurement system shown in FIG. 1.

FIG. 1 is a block diagram illustrating a health measurement system for a vehicle driver according to an embodiment of the present disclosure. FIG. 2 is a circuit diagram illustrating constituent elements of the health measurement system shown in FIG. 1.

Referring to FIG. 1, a health measurement system for a driver of a vehicle may include a controller 200 interacting with an ignition switch 100 of the vehicle, and a telematics terminal 300 and an Internet of Things (IoT) device 400 which communicate with the controller 200.

The controller 200 is an electric circuitry that executes instructions of software which thereby performs various functions described hereinafter.

Referring to FIG. 2, the ignition switch 100 may generate a starter signal (St) when receiving a starting signal from the driver, and may be in a ready mode (Sr) when receiving no starting signal from the driver. The starter signal (St) is transmitted to a starter relay 20, and the starter relay 20 supplies a battery voltage to the controller 200 and the starter motor 10, such that the controller 200 may start operation.

The controller 200 may perform health scanning to check the presence or absence of an abnormal health condition of the driver at an ignition start time of the vehicle or during traveling of the vehicle. In order to perform health scanning only at a necessary time of the health scanning, the controller 200 may determine whether a necessary condition (i.e., a requirement) of health scanning is satisfied.

As described above, if an output signal of the ignition switch (St) is input to the controller 200 when the vehicle starts operation, the controller 200 may determine whether the necessary condition of the driver's health scanning is satisfied by analyzing traveling environment information. A detailed description thereof will be given later.

In this case, if the necessary condition of the health scanning is achieved, the controller 200 may perform health scanning only at a necessary time.

If the health scanning necessary condition is satisfied as described above, the controller 200 may output a starter motor drive signal (Vs) and a health scanning execution signal (Vg), and may inform the driver of the result of health scanning as soon as the vehicle starts operation, as denoted by "Result Alarm" in FIG. 2.

On the other hand, if the health scanning necessary condition is not satisfied, a controller 200 may output only the starter motor drive signal (Vd, such that the vehicle starts ignition without execution of health scanning.

The health measurement system for the vehicle driver according to the present disclosure can determine whether a health scanning necessary condition is satisfied at an ignition start time of the vehicle or during traveling of the vehicle. The health measurement system can perform health scanning of the driver only at a proper time such that it can remove driver's negative thoughts caused by repeated physical scanning and can recognize a health condition of the driver only at a substantially necessary time, resulting in guarantee of safe driving.

Figure 3:
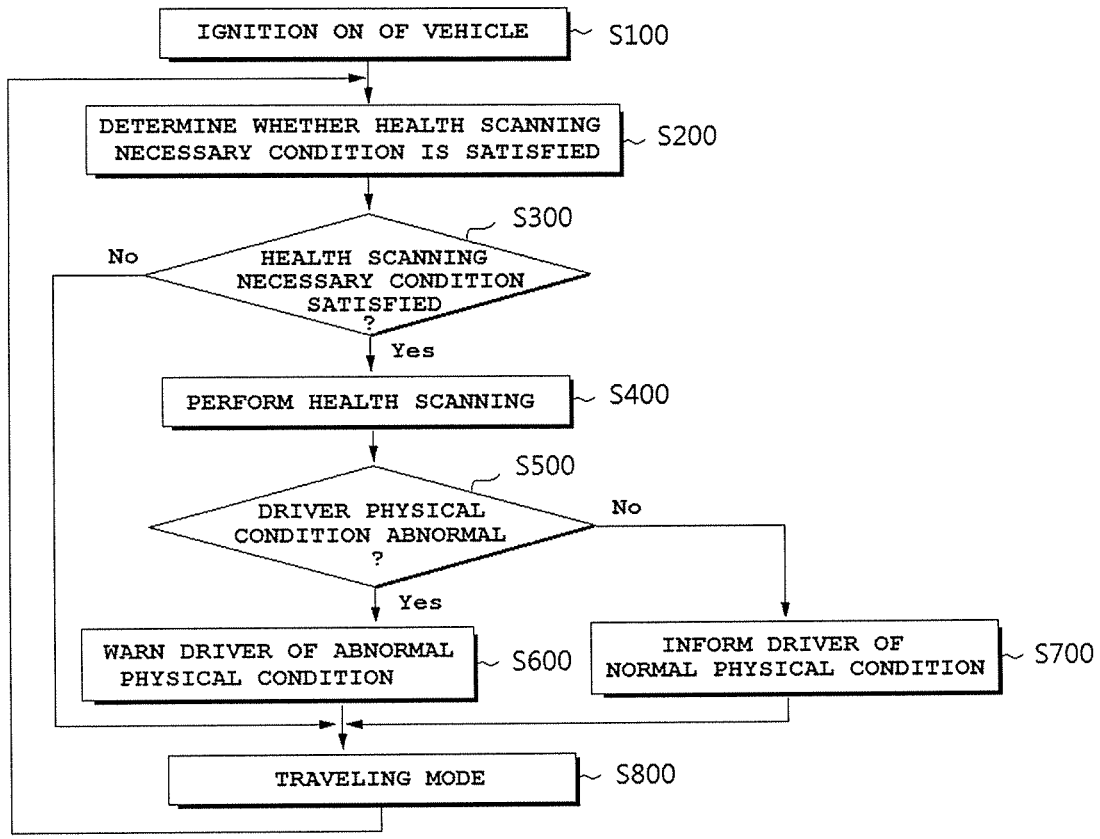
FIG. 3 is a flowchart illustrating a warning method using a health measurement system for a vehicle driver according to an embodiment of the present disclosure.

FIG. 3 is a flowchart illustrating a warning method using a health measurement system for a vehicle driver according to an embodiment of the present disclosure. FIG. 4 is a flowchart illustrating a warning method using a health measurement system for a vehicle driver according to another embodiment of the present disclosure.

A warning method using the above-mentioned health measurement system for the vehicle driver will hereinafter be described.

Referring to FIG. 3, the warning method using the health measurement system 1 for the vehicle driver may include starting ignition of the vehicle in which the driver rides (S100).

If the vehicle starts ignition (S100), the controller 200 may determine whether a necessary condition of health scanning of the driver is satisfied by analyzing traveling environment information (S200).

That is, the step S200 of determining whether the health scanning necessary condition is satisfied may be performed by analyzing traveling environment information from among various kinds of information that is input to the vehicle at an ignition start time of the vehicle. In this case, the traveling environment information may include at least one of a date and time where the vehicle starts ignition, an estimated driving time, a traveling time, a current time, a traveling route, a traffic situation, etc.

For example, the traveling environment information may be stored in the telematics terminal 300 of the vehicle, and may use information stored in the IoT device 400. The IoT device 400 may communicate with the telematics terminal 300, such that the IoT device 400 may also retrieve the traveling environment information contained in the IoT device 400 from the telematics terminal 300.

In this case, the IoT device 400 may include at least one of a smartphone, a health band, a smart watch, etc.

The smartphone may include various applications, such that it can store a schedule of a user (or driver), navigation traveling information, health information, sleep time record, etc. therein. The smartphone may communicate with other IoT devices 400, such as a health band and a smart watch, and may store or output various kinds of information input to the IoT devices 400.

The health band may refer to a health measurement band worn on the driver's body, for example, a wrist, a neck, a finger, a foot, etc. of the driver. The health band may include various sensors, may measure various parameters, for example, the number of footsteps or footfalls of the driver, a body temperature, a pulse rate, a heart rate, a fatigue level, a sleep time record, etc. using the various sensors, such that the health band may inform the driver of the measurement result or may share the measurement result with the smartphone by communicating with the smartphone.

The smart watch may be a communication device having a function of a watch wearable on the driver's wrist, and may include not only additional functions associated with the smartphone but also other sensors. Therefore, the smart watch may measure the number of footsteps of the driver, a body temperature, a pulse rate, a heart rate, a fatigue level, and a sleep time record using the other sensors, may inform the driver of the measurement result, or may share the measurement information with the smartphone by communicating with the smartphone.

The step S200 of determining whether the health scanning necessary condition is satisfied may include receiving information from the telematics terminal 300 or the IoT device 400, and controlling the controller 200 to determine the received information.

For example, the step S200 of determining whether the health scanning necessary condition is satisfied may include determining whether at least one of a first condition in which a date contained in the traveling environment information is changed at an ignition ON time of the vehicle, a second condition in which at least 4 hours have elapsed after an ignition OFF time of the vehicle, a third condition in which the vehicle is scheduled to travel at least 2 hours, a fourth condition in which a section having less cognitive load or less stimulus is contained in a traveling route, and a fifth condition in which a congested section is contained in the traveling route is satisfied.

In more detail, if the ignition start signal of the vehicle is input to the controller 200 (S100), the controller 200 may compare a current date where the driver turns on the ignition switch with the latest ignition ON date of the vehicle. If the current date is different from the latest ignition ON date, the controller 200 may determine that health scanning of the driver is needed. That is, if the current ignition ON date of the vehicle is different from the latest ignition ON date, this means that a necessary condition of the health scanning is satisfied because there is a possibility of causing a change in the driver's health condition. In addition, the date in which the necessary condition of the health scanning is satisfied may further include either a date to which a daylight saving time (DST) or summer time (ST) is applied, or the following date after holidays.

If the ignition ON time at which the driver turns on the ignition switch of the vehicle is identical to a specific time located behind a predetermined time after the vehicle stops ignition, the controller 200 may determine that health scanning of the driver is needed. For example, the predetermined time may be at least 4 hours. If at least 4 hours have elapsed after the ignition OFF time of the vehicle, the controller 200 may estimate occurrence of the change of a health condition of the driver, and may thus determine that health scanning of the driver is needed. For example, the predetermined time may be set to at least 3 hours, at least 5 hours, or the like, and may also be set to another time as necessary.

The controller 200 may analyze a regular driving pattern of the driver, for example, commuting hours (e.g., an attendance time and a closing time), through information contained in the driver's smartphone or navigation device of the vehicle, such that the controller 200 may estimate a total driving time to be consumed for each destination. If the estimated driving time is at least 2 hours, it is expected that the driver will drive the vehicle for a long time, such that the controller 200 may determine that health scanning of the driver is needed.

If a section (e.g., desert road or expressway) having less cognitive load or less stimulus for at least a predetermined time (e.g., at least 30 minutes) is contained in the traveling route of the vehicle, the driver's concentration is deteriorated and there is a higher possibility of accidents due to drowsy driving, such that the controller 200 may determine that health scanning of the driver is needed.

Even when a current traffic situation is a traffic congestion situation in which traffic congestion is prolonged for at least a predetermined time (e.g., 30 minutes), the driver's concentration is also deteriorated and there is a high possibility of accidents such as drowsy driving, such that the controller 200 may also determine that health scanning of the driver is needed.

In the step S200 of determining whether the health scanning necessary condition is satisfied, the controller 200 determines that health scanning of the driver is needed (i.e., a current situation satisfies a necessary condition) by analyzing the traveling environment information (S300), and performs health scanning of the driver (S400). If the necessary condition is not satisfied in the step S200 for determining whether the health scanning necessary condition is satisfied, the controller 200 determines that health scanning need not be performed, does not perform health scanning, and continuously performs a traveling mode (S800) after the ignition start signal is applied to the vehicle.

In the health scanning execution step S400, a physical condition of the driver is scanned through information input to either the telematics terminal 300 of the vehicle or the IoT device 400. The IoT devices 400, such as a smartphone, a health band, and a smart watch, and the telematics terminal 300 may simultaneously store the schedule of the user (or driver), navigation traveling information, health information, sleep time record, etc. Therefore, the controller 200 may check a current physical condition of the driver by scanning the number of footsteps, a body temperature, a pulse rate, a heart rate, a fatigue level, a sleep time record, etc.

As described above, it is determined whether a physical condition of the driver is normal or abnormal through the health scanning execution result S400. For example, if the scanned sleep time is shorter than a normal sleep time, or if the heart rate or the body temperature of the driver deviates from a normal range, the controller 200 may determine that a physical condition of the driver is an abnormal physical condition inappropriate for vehicle driving.

If the abnormal physical condition of the driver is decided (S500), the controller 200 may display a warning message indicating the abnormal physical condition of the driver (S600). If the driver's physical condition is normal (S500), the controller 200 may display a message indicating a normal physical condition of the driver (S700).

In this case, the step S600 of displaying the warning message indicating the abnormal physical condition of the driver may include at least one of visually displaying the warning message through the telematics terminal 300 (more specifically, a display or a speaker) and audibly displaying the warning message through the telematics terminal 300 (more specifically, a display or a speaker). Here, the warning message may display at least one of the number of footsteps, the body temperature, the pulse rate, the heart rate, the fatigue level, and the sleep time record of the driver using numerals or symbols, and may include content needed to determine whether a physical condition of the driver is normal or abnormal.

Prior to step S400 for performing the driver's health scanning, if the health scanning necessary condition is satisfied, health scanning is notified to the driver, such that the driver may feel consciousness and may directly decide whether to perform the health scanning.

As shown in FIG. 4, even when the vehicle is traveling (S110) (see the traveling mode step S800 of FIG. 3) after being started up, the health scanning necessary condition is determined according to situations, the health scanning is performed according to the determined result, and the health scanning result is displayed.

In the step S200 for determining whether the health scanning necessary condition is satisfied during traveling of the vehicle, the controller 200 may include at least one of a traveling time, a current time, a traveling route, and a traffic situation from among traveling environment information.

Differently from the term "traveling environment information" used in the aforementioned embodiment, the traveling environment information used in this embodiment may exclude special situations encountered during ignition starting of the vehicle, and may include factors in which various parameters (e.g., a fatigue level, a health condition change, etc. of the driver) are further considered.

For example, the traveling environment information used in this embodiment may indicate whether at least one of a first condition in which the vehicle travels for at least a predetermined time (e.g., 30 minutes) at night, a second condition in which the vehicle is scheduled to travel for at least 2 hours, a third condition in which a section having less cognitive load or less stimulus is contained in the traveling route, and a fourth condition in which a congested section is contained in the traveling route is satisfied.

In accordance with the above-mentioned traveling environment information, factors capable of causing change of a health condition of the driver during traveling of the vehicle are determined, such that the controller 200 may determine that health scanning of the driver is needed.

In the step S200 of determining whether the health scanning necessary condition is satisfied, the controller 200 may determine that health scanning of the driver is needed by analyzing traveling environment information (S300). If the controller 200 determines that health scanning of the driver is needed by analyzing traveling environment information (S300), the controller 200 may perform health scanning of the driver (S400). In the step S200 of determining whether the health scanning necessary condition is satisfied, the health scanning necessary condition is not satisfied, the controller 200 determines that health scanning of the driver need not be performed, and may continuously perform the traveling mode (S800) after the vehicle starts ignition without performing health scanning.

Prior to step S400 of performing driver health scanning, if the health scanning necessary condition is satisfied, the driver is notified of health scanning, such that the driver may feel awake and may directly decide whether to perform the health scanning.

In the health scanning execution step S400, a physical condition of the driver is scanned through information input to the telematics terminal 300 of the vehicle or the IoT device 400. The IoT device 400, such as a smartphone, a health band, or a smart watch, and the telematics terminal 300 may simultaneously store the schedule of the user (or driver), navigation traveling information, health information, sleep time record, etc. Therefore, the controller 200 may check a current physical condition of the driver by scanning the number of footsteps, a body temperature, a pulse rate, a heart rate, a fatigue level, a sleep time record, etc.

As described above, it is determined whether a physical condition of the driver is normal or abnormal through the health scanning execution result S400. For example, if the scanned sleep time is shorter than a normal sleep time, or if the heart rate or the body temperature of the driver deviates from a normal range, the controller 200 may determine that a physical condition of the driver is an abnormal physical condition inappropriate for vehicle driving.

If the abnormal physical condition of the driver is decided (S500), the controller 200 may display a warning message indicating the abnormal physical condition of the driver (S600). If the driver's physical condition is normal (S500), the controller 200 may display a message indicating a normal physical condition of the driver (S700).

In this case, the step S600 of displaying the warning message indicating the abnormal physical condition of the driver may include at least one of visually displaying the warning message through the telematics terminal 300 (more specifically, a display or a speaker) and audibly displaying the warning message through the telematics terminal 300 (more specifically, a display or a speaker).

Here, the warning message may display at least one of the number of footsteps, the body temperature, the pulse rate, the heart rate, the fatigue level, and the sleep time record of the driver using numerals or symbols, and may include content needed to determine whether a physical condition of the driver is normal or abnormal.

After the displaying step S600, the step S200 of determining whether the health scanning necessary condition is satisfied is performed again, such that health scanning can be performed only at a necessary time. The above-mentioned processes may be repeatedly performed.

As described above, the health measurement system for the vehicle driver and the warning method using the same according to the embodiments of the present disclosure can determine the presence or absence of an abnormal health condition of the driver by scanning a physical condition of the driver at an ignition start time of the driver or at a proper time during driving of the vehicle, can inform the driver of the determined result, can warn the driver of the abnormal health condition when there is a high possibility of causing accidents, thereby arousing a driver's attention in safe driving.

The health measurement system and the warning method using the same according to the embodiments of the present disclosure can perform health scanning of the driver only at a proper time by analyzing traveling environment information, can remove driver's negative thoughts caused by repeated physical scanning, and can recognize a health condition of the driver only at a substantially necessary time, resulting in guarantee of safe driving.

Features, structures, effects, and the like as described above in the embodiments are included in at least one embodiment of the present disclosure and should not be limited to only one embodiment. In addition, the features, structures, effects, and the like described in the respective embodiments may be combined or modified even with respect to the other embodiments by those skilled in the art. Accordingly, contents related to these combinations and modifications should be construed as within the scope of the present disclosure.

As is apparent from the above description, the health measurement system for a vehicle driver and a warning method using the same according to the embodiments of the present disclosure can determine whether the driver has an abnormal healthy condition by scanning a physical condition of the driver at a driving start time of the vehicle or at a proper time during driving of the vehicle, and can warn the driver of his or her abnormal health condition when there is a high possibility of causing accidents, thereby arousing a driver's attention in safe driving.

The health measurement system for a vehicle driver and a warning method using the same according to the embodiments of the present disclosure can perform health scanning of the driver only at a proper time by analyzing traveling environment information, can remove driver's negative thoughts caused by repeated physical scanning, and can recognize a health condition of the driver only at a substantially necessary time, resulting in guarantee of safe driving.

It will be apparent to those skilled in the art that various modifications and variations can be made in the present disclosure without departing from the spirit or scope of the invention. Therefore, the above-mentioned detailed description must be considered only for illustrative purposes instead of restrictive purposes. The scope of the present disclosure must be decided by a rational analysis of the claims, and all modifications within equivalent ranges of the present disclosure are within the scope of the present disclosure.

What is claimed is:

1. A health measurement system for a driver of a vehicle, comprising:
   an ignition switch;

a starter motor;

an Internet of Things (IoT) device;

a controller communicatively connected to the TOT device and configured to determine a necessary condition of health scanning of the driver, and perform the health scanning according to a result of the determination; and a starter relay configured to supply a battery voltage to the controller and the starter motor, wherein the controller analyzes traveling environment information when the ignition switch is turned on, determines whether the necessary condition of the health scanning is satisfied, and performs the health scanning only when the necessary condition of the health scanning is satisfied, and wherein the controller determines whether, from among the traveling environment information, at least one of a first condition in which a date is changed when the vehicle starts ignition, a second condition in which a predetermined time has elapsed after the vehicle stops ignition, a third condition in which the vehicle is scheduled to travel for at least a predetermined travel time, a fourth condition in which a section having less cognitive load or less stimulus is contained in the traveling route, and a fifth condition in which a congested section is contained in the traveling route is satisfied.

2. The health measurement system according to claim 1, wherein the traveling environment information includes at least one of a date and time at which the vehicle starts ignition, an estimated driving time, a traveling time, a current time, a traveling route, and a traffic situation.

3. The health measurement system according to claim 1, wherein the IoT device includes at least one of a smartphone, a health band, and a smart watch.

4. The health measurement system according to claim 2, wherein:

when determining whether the necessary condition of the health scanning is satisfied, if any one of the traveling environment information is satisfied, a determination is made that the health scanning is needed, and if any one of the traveling environment information is not satisfied, a determination is made that the health scanning need not be performed.

5. The health measurement system according to claim 4, wherein:

the controller interacts with an ignition switch, and determines whether the necessary condition of the health scanning is satisfied during ignition starting of the vehicle or during traveling of the vehicle.

6. The health measurement system according to claim 5, wherein:

if the necessary condition of the health scanning is satisfied, the controller pre-informs the driver of the health scanning, and then executes the health scanning for the driver.

7. The health measurement system according to claim 6, wherein the health scanning is executed in consideration of at least one of the number of footsteps of the driver, a body temperature, a pulse rate, a heart rate, a fatigue level, and a sleep time record, which are stored in a telematics terminal or the IoT device.

8. The health measurement system according to claim 7, wherein the controller determines whether a physical condition of the driver is normal or abnormal through an execution result of the health scanning, visually or audibly displays a result of the health scanning through the telematics terminal.

9. The health measurement system according to claim 8, wherein the display result of the health scanning displays at least one of the number of footsteps of the driver, a body temperature, a pulse rate, a heart rate, a fatigue level, and a sleep time record using numerals or symbols, and includes content for determining whether a health condition of the driver is normal or abnormal.

10. A warning method using a health measurement system for a driver of a vehicle, the health measurement system including a controller and an Internet of Things (IoT) device that are communicatively connected each other, the warning method comprising steps of:

receiving, by the controller, an ignition start signal of the vehicle;

analyzing, by the controller, traveling environment information, and determining whether a necessary condition of health scanning for the driver is satisfied;

if the necessary condition of the health scanning is satisfied, executing, by the controller, health scanning for the driver;

determining, by the controller, whether a physical condition of the driver is normal or abnormal through an execution result of the health scanning; and if the physical condition of the driver is abnormal, displaying, by a telematics terminal of the vehicle, a warning message indicating the physical condition of the driver is abnormal, and if the physical condition of the driver is normal, displaying a message indicating the physical condition of the driver is normal, wherein the traveling environment information includes at least one of a date and time at which the vehicle starts ignition, an estimated driving time, a traveling route, and a traffic situation, wherein the IoT device includes at least one of a smartphone, a health band, and a smart watch, and wherein the step of determining whether the necessary condition of the health scanning is satisfied includes:

determining whether, from among the traveling environment information, at least one of a first condition in which a date is changed when the vehicle starts ignition, a second condition in which a predetermined time has elapsed after the vehicle stops ignition, a third condition in which the vehicle is scheduled to travel for at least a predetermined travel time, a fourth condition in which a section having less cognitive load or less stimulus is contained in the traveling route, and a fifth condition in which a congested section is contained in the traveling route is satisfied.

11. The method according to claim 10, wherein the step of determining whether the health scanning necessary condition is satisfied includes:

if any one of the first to fifth conditions is satisfied, determining that the health scanning is needed; and if any one of the first to fifth conditions is not satisfied, determining that the health scanning need not be executed.

12. The method according to claim 11, wherein the health scanning is executed in consideration of at least one of the number of footsteps of the driver, a body temperature, a pulse rate, a heart rate, a fatigue level, and a sleep time record, which are received from the IoT device.

13. The method according to claim 12, wherein:

the traveling environment information is stored in a telematics terminal of the vehicle; and the IoT device communicates with the telematics terminal.

14. The method according to claim 13, wherein the step of displaying a warning message includes at least one of visually displaying the warning message through the telematics terminal and audibly displaying the warning message through the telematics terminal, wherein the step of displaying a warning message includes:

displaying at least one of the number of footsteps of the driver, a body temperature, a pulse rate, a heart rate, a fatigue level, and a sleep time record using numerals or symbols, and including content for determining whether the physical condition of the driver is normal or abnormal.

15. The method according to claim 14, further comprising:

prior to the step of executing health scanning of the driver, if the necessary condition of the health scanning is satisfied, pre-informing the driver of the health scanning.

16. A warning method using a health measurement system of a driver of a vehicle, the health measurement system including a controller and a telematics terminal that are communicatively connected each other, the warning method comprising:

allowing the vehicle to operate in a traveling mode;

determining, by the controller, whether a necessary condition of health scanning of the driver is satisfied by analyzing traveling environment information;

if the necessary condition of the health scanning is satisfied, executing, by the controller, health scanning of the driver;

determining, by the controller, whether a physical condition of the driver is normal or abnormal through an execution result of the health scanning; and if the physical condition of the driver is abnormal, displaying, by the telematics terminal, a warning message indicating the physical condition of the driver is abnormal, and if the physical condition of the driver is normal, displaying a message indicating the physical condition of the driver is normal, wherein the traveling environment information includes at least one of a traveling time, a current time, a traveling route, and a traffic situation, after the step of displaying a warning message indicating the physical condition of the driver is abnormal or the step of displaying a message indicating the physical condition of the driver is normal, the warning method further comprises re-performing the step of determining whether a necessary condition of health scanning is satisfied, and wherein the step of determining whether a necessary condition of health scanning is satisfied includes:

determining whether, from among the traveling environment information, at least one of a first condition in which the vehicle travels for at least a predetermined time at night, a second condition in which the vehicle is scheduled to travel for at least a predetermined travel time, a third condition in which a section having less cognitive load or less stimulus is contained in the traveling route, and a fourth condition in which a congested section is contained in the traveling route is satisfied.

17. The method according to claim 16, wherein the step of determining whether a necessary condition of health scanning is satisfied includes:

if any one of the first to fourth conditions is satisfied, determining that the health scanning is needed; and if any one of the first to fourth conditions is not satisfied, determining that the health scanning need not be executed.

18. The method according to claim 17, further comprising:

prior to the step of executing health scanning of the driver, if the necessary condition of the health scanning is satisfied, pre-informing the driver of the health scanning.

* * * * *